| United States Patent [19] | [11] Patent Number: 4,874,879 |
| Lauritzen et al. | [45] Date of Patent: Oct. 17, 1989 |

[54] PROCESS FOR STARTING-UP AN ETHYLENE OXIDE REACTOR

[75] Inventors: Ann M. Lauritzen, Houston; David S. Baker, Sugarland; Margot H. Christiansen, Houston; Beamon M. Johnson, Brookshire; John G. Schuren, Houston, all of Tex.

[73] Assignee: Shell Oil Company, Houston, Tex.

[21] Appl. No.: 224,049

[22] Filed: Jul. 25, 1988

[51] Int. Cl.$^4$ .......................................... C07D 301/10
[52] U.S. Cl. ..................................................... 549/536
[58] Field of Search .............................. 549/534, 536

[56] References Cited

U.S. PATENT DOCUMENTS

| 4,226,782 | 10/1980 | Hayden et al. | 549/534 |
| 4,409,394 | 10/1983 | Vangermain et al. | 549/534 |
| 4,471,071 | 9/1984 | Rebsdat et al. | 549/534 X |

Primary Examiner—W. J. Shine

[57] ABSTRACT

This invention relates to a process for starting up a fixed bed ethylene oxide reactor containing a catalyst comprising silver, alkali metal promoter and rhenium co-promoters supported on an alumina carrier which process comprises heating the reactor to slightly below normal operating conditions, passing an ethylene containing gas over the catalyst at a flow rate of about 20% of design, adding a chlorohydrocarbon moderator to the gas passing over the catalyst and after approximately 1 cubic centimeters of moderator (basis liquid) per cubic foot of catalyst has been added, then adding oxygen to the gas passing over the catalyst to initiate the ethylene oxidation reaction and subsequently raising the reactor temperature and gas flow rates to operating conditions.

17 Claims, No Drawings

PROCESS FOR STARTING-UP AN ETHYLENE OXIDE REACTOR

FIELD OF THE INVENTION

This invention relates to a process for starting-up a fixed bed ethylene oxide reactor containing a catalyst comprising silver, alkali metal promoter and rhenium co-promoter supported on an alpha alumina carrier.

BACKGROUND OF THE INVENTION

A number of commercial ethylene oxide processes utilize a tube sheet reactor for converting ethylene to ethylene oxide. This fixed bed reactor typically utilizes a silver-based catalyst which has been supported on a porous support and which is typically promoted with an alkali metal promoter. The shell side of the ethylene oxide reactor typically utilizes a high temperature coolant to remove the heat generated by the oxidation reaction. Under operating conditions a chlorohydrocarbon moderator is utilized to control the oxidation reaction.

The usual practice for starting up new silver-based ethylene oxide catalysts in a commercial plant is to first add ethylene and diluent gas, then slowly introduce oxygen to get the reaction started, then to gradually introduce chlorohydrocarbon moderator to control the reaction after it is producing enough heat to become self-sustaining. For the traditional silver-based, alkali metal promoted supported catalyst, the chlorohydrocarbon moderator serves to decrease the activity (i.e., raise the temperature required to obtain a given conversion level) while increasing selectivity to ethylene oxide. When utilizing conventional alkali-promoted, supported silver catalysts, the catalysts are very active at normal stat-up temperatures. Chlorohydrocarbon moderator levels are introduced after start-up to control the high catalyst activity to reduce the conversion level, and to prevent a "run away".

SUMMARY OF THE INVENTION

This invention relates to a process for starting up a fixed bed ethylene oxide reactor containing a catalyst comprising silver, an alkali metal promoter and a rhenium co-promoter supported on an alumina carrier which process comprises a) heating the reactor to slightly below its normal operating temperature, b) passing an ethylene-containing gas over the catalyst, c) adding a halohydrocarbon moderator to the gas passing over the catalyst and after about 0.1 to about 10 cubic centimeters of the moderator (basis liquid) per cubic foot of the catalyst has been added, d) adding oxygen to the gas passing over the catalyst to start the oxidation reaction and raising the reactor temperature and gas flow rates to operating conditions. This process is applied to new or fresh catalysts, as well as to used catalysts that have been subjected to a prolonged shut-down period.

DESCRIPTION OF THE PREFERRED EMBODIMENTS

Catalyst

The catalyst that is used in the fixed bed reactor that is started up by the process of the instant invention comprises silver, alkali metal promoter and rhenium co-promoter supported on an alumina carrier. Other moderators and promoters may be utilized but the key to the instant invention is the use of a catalyst containing the rhenium as a promoter. These catalyst compositions are fully described in U.S. patent application Ser. No. 926,025, filed Oct. 31, 1986 now U.S. Pat. No. 4,766,105; U.S. patent application Ser. No. 926,026 filed Oct. 31, 1986, now U.S. Pat. No. 4,761,394 and application Ser. No. 184,531, filed Apr. 20, 1988, now U.S. Pat. No. 4,808,738 all of which are incorporated by reference herein.

The catalysts used in the instant process comprise a catalytically effective amount of silver, a promoting amount of alkali metal and a promoting amount of rhenium. Preferably the major amount of alkali metal promoter present is a higher alkali metal selected from potassium, rubidium, cesium and mixtures thereof. Most preferably the alkali metal is cesium. Combinations of alkali metals, such as cesium and lithium are quite suitable. Concentrations of alkali metal (measured as the metal) between about 10 and 3000 ppm, preferably between about 15 and about 2000 ppm and more preferably between about 20 and about 1500 ppm by weight of total catalyst are desirable. The rhenium promoter concentration will range from about 0.1 to about 10, preferably from about 0.2 to about 5 millimoles, measured as the element, per kilogram of total catalyst. Other co-promoters may be present. Desired co-promoters are selected from compounds of sulfur, molybdenum, tungsten, chromium and mixtures thereof. Particularly preferred as a co-promoter is sulfate. Co-promoter concentrations will range from about 0.1 to about 10, preferably from about 0.2 to about 5 millimoles, measured as the element, per kilogram of total catalyst.

The Process

The process of the instant invention is applied to new catalysts as well as to aged catalysts that, due to a plant shut-down, have been subjected to a prolonged shut-in period.

When new catalysts are utilized it has been found useful to subject these catalysts to a high temperature with nitrogen gas passing over the catalyst. The high temperature converts a significant portion of the organic nitrogen compounds used in the manufacture of the catalyst to nitrogen-containing gases which are swept up in the nitrogen stream and removed from the catalyst. Typically, the catalyst is loaded into the tube reactor and by utilizing a coolant heater, the temperature of the reactor is brought up to within 10° F. to 100° F., preferably to 20° F. to 50° F. below the normal operating conditions. Temperatures closer to the normal operating temperatures can be utilized, but in most commercial operations the coolant heater is not sized large enough to bring the reactor up to full operating temperatures. In general, the reactor is heated to a temperature between about 400° F. and 475° F. A nitrogen flow, if utilized, is then passed over the catalyst at a flow rate typically between about 5 to about 40% of the design flow rate, preferably between about 15 and about 25% of the design flow rate. The nitrogen flow may be initiated before reactor heatup, during reactor heatup or after the reactor has reached the desired temperature. The nitrogen gas is typically passed over the catalyst for a period of time ranging from about ½ of a day to about 7 days. During this purge time the nitrogen stream is monitored for nitrogen-containing decomposition products from the catalysts. The startup of used catalysts may or may not require the use of nitrogen, but it is frequently used. When nitrogen is not utilized, the reactor may be pressurized with ethylene, methane or other non-oxidizing gas.

After the nitrogen-containing decomposition products have been removed to a suitable low level, generally less than about 10 ppm, the recycle loop to the ethylene oxide reactor is then pressurized with ethylene and a suitable ballast gas such as methane in preparation for a start up. A gas flow rate of between about 5 to about 40% of design rate, preferably from about 15 to about 25% of design rate is maintained over the reactor.

A chlorohydrocarbon moderator is then added to the recycle gas stream being fed to the ethylene oxide reactor. The amount of chlorohydrocarbon moderator is added slowly over a period of several hours until approximately 0.1 to about 10 cubic centimeters, preferably 0.5 to about 5, and more preferably 0.75 to about 2 cubic centimeters of chlorohydrocarbon moderator (basis liquid) per cubic foot of catalyst in the reactor bed has been added to the recycle feed loop. When fresh catalyst is used, it contains no chloride on its silver surfaces and hence the initial chlorohydrocarbon that is added to the recycle feed stream will be absorbed by the catalyst until the catalyst reaches a steady state at which point the chlorohydrocarbon moderator will begin to build up in the recycle feed stream to a steady level. Suitable chlorohydrocarbons used as moderators comprise the $C_1$ to $C_8$ chlorohydrocarbons, that is compounds comprising hydrogen, carbon and chlorine. Preferably these chlorohydrocarbons are $C_1$ to $C_4$ chlorohydrocarbons and most preferably they are $C_1$ and $C_2$ chlorohydrocarbons. The chlorohydrocarbons may be optionally substituted with fluorine. Illustrative examples of these moderators include methyl chloride, ethyl chloride, ethylene dichloride, vinyl chloride and mixtures thereof. Preferred moderators are ethyl chloride, ethylene dichloride and vinyl chloride, particularly ethyl chloride. The moderator is added to the reactor during this step preferably during a period of time ranging from about 1 to about 10 hours, preferably 2 to about 6 hours. These times, however, are not critical and shorter or longer periods can be used.

After the chlorohydrocarbon moderator has been fed to the catalyst in the above-defined range, oxygen is then added to the recycle feed stream at initially from about 5 to about 40% of design rate, preferably from about 15 to about 25% of design rate. Reaction initiation will occur within a few minutes of the addition of the oxygen, after which point the oxygen feed to the reactor, the feed gas to the reactor and the reactor temperature are raised to approximately the design conditions over a period of time ranging from about 15 mins. to about 6 hrs., preferably from about 30 mins. to about 4 hrs.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention as defined by the instant specification and claims.

The following example is provided as a means to illustrate the process of the instant invention and is not to be construed as limiting the invention.

EXAMPLE

An alumina supported silver catalyst containing as promoters cesium, lithium, rhenium and sulfate was loaded into a fixed bed tubular ethylene oxide reactor. The reactor was heated to about 430° F. utilizing the reactant coolant heaters during which nitrogen gas was circulated through the reactor at about 25% of design flow rate. Nitrogen flow was continued for about 24 hrs., at which point the flow was stopped. The reactor was checked for ammonia gas, which is a decomposition product of some of the organonitrogen compounds used in preparing the catalyst, and it was found that ammonia was less than about 5 ppm. Pressurization of the reactor recycle loop reactor with ethylene and methane in preparation for start up was initiated. A gas flow rate of about 20% of design flow rate was maintained to the reactor.

Ethyl chloride was then added to the gas stream flowing over the catalyst. The ethyl chloride target flow rate to the reactor was about 400 cc per hr. The total dosage applied to the catalyst in the reactor prior to oxygen addition was about 1.3 cubic centimeters of liquid ethyl chloride per cubic foot of catalyst.

At about 3 hrs. and 45 mins. after the start of the ethyl chloride addition, oxygen was then added at about 17% of design flow rate at a coolant temperature now of about 450° F. Reaction initiated within 2 mins. of oxygen addition with about 1% oxygen in the feed. The oxygen flow rate was quickly increased to about 70% of design flow rate during the first 20 mins. after start up. During this period the feed gas flow was increased from 25% to about the maximum. Maximum catalyst temperature to this point was about 525° F. After about 1 hr. after oxygen initiation, the reactor coolant temperature reached about 480° F. Minor adjustments to the reactor conditions were made over the next several days to bring the catalyst to its optimum operating conditions.

We claim:

1. A process for starting up a fixed bed ethylene oxide reactor containing a catalyst comprising silver, alkali metal promoter and rhenium co-promoter supported on an alumina carrier, which process comprises:
    (a) heating the reactor to a temperature between about 400° F. and 475° F.,
    (b) passing an ethylene-containing gas over the catalyst in the reactor at a flow rate between about 5 to about 40 percent of the design flow rate,
    (c) adding a chlorohydrocarbon moderator to the gas passing over the catalyst and after between about 0.1 to about 10 cubic centimeters of moderator (basis liquid) per cubic foot of catalyst has been added,
    (d) adding oxygen to the gas passing over catalyst, and raising the reactor temperature and gas flow rates to operating conditions.

2. The process of claim 1 wherein in step b) the ethylene-containing gas is passed over the reactor at a flow rate between about 15 to about 25 percent of the design flow rate.

3. The process of claim 1 wherein in step b) the ethylene-containing gas also contains nitrogen and methane.

4. The process of claim 1 wherein the chlorohydrocarbon moderator is a $C_1$ to $C_8$ chlorohydrocarbon.

5. The process of claim 4 wherein the chlorohydrocarbon moderator is a $C_1$ to $C_4$ chlorohydrocarbon.

6. The process of claim 5 wherein the chlorohydrocarbon moderator is a $C_1$ or $C_2$ chlorohydrocarbon.

7. The process of claim 6 wherein the chlorohydrocarbon moderator is selected from the group consisting of methyl chloride, ethyl chloride, ethylene dichloride, vinyl chloride and mixtures thereof.

8. The process of claim 1 wherein in step (c) from about 0.5 to about 5 cubic centimeters of moderator per cubic feet of catalyst is added.

9. The process of claim 8 wherein in step (c) from about 0.75 to about 2 cubic centimeters of moderator per cubic feet of catalyst has been added.

10. The process of claim 1 wherein in step (c) the moderator is added over a period of time ranging from about 1 to about 10 hours.

11. The process of claim 10 wherein in step (c) the moderator is added over a period of time ranging from about 2 to about 6 hours.

12. The process of claim 1 wherein in step (d) the reactor temperature and gas flow rates are raised to operating conditions over a period of time after the start of the oxygen addition ranging from about 15 minutes to about 6 hours.

13. The process of any one of claims 1–12 wherein nitrogen gas is passed over the catalyst prior to passing ethylene-containing gas of step (b) over the catalyst.

14. The process of claim 13 wherein the nitrogen gas is passed over the catalyst at a flow rate of between about 5 to about 40 percent of design flow rate.

15. The process of claim 14 wherein the nitrogen gas is passed over the catalyst at a flow rate of between about 15 to about 25 percent of design flow rate.

16. The process of claim 14 wherein the nitrogen is passed over the catalyst for a period of time ranging from about ½ to about 7 days.

17. The process of claim 15 wherein the nitrogen is passed over the catalyst for a period of time ranging from about ½ to about 7 days.

* * * * *